US009145221B2

(12) United States Patent
Kalyanpur et al.

(10) Patent No.: US 9,145,221 B2
(45) Date of Patent: Sep. 29, 2015

(54) CONVERTIBLE TWO COMPARTMENT CONTAINER

(75) Inventors: Anil Kalyanpur, Edison, NJ (US); Richard Suhr, Seaside Heights, NJ (US)

(73) Assignee: La Prairie, Inc., New York, NY (US)

( * ) Notice: Subject to any disclaimer, the term of this patent is extended or adjusted under 35 U.S.C. 154(b) by 269 days.

(21) Appl. No.: 13/425,173

(22) Filed: Mar. 20, 2012

(65) Prior Publication Data

US 2013/0248391 A1 Sep. 26, 2013

(51) Int. Cl.
*B67D 7/74* (2010.01)
*B67D 7/70* (2010.01)
*B65D 1/04* (2006.01)
*B65D 21/02* (2006.01)
*B65D 43/14* (2006.01)
*B65B 29/10* (2006.01)
*B65D 81/32* (2006.01)
*B65D 35/42* (2006.01)

(52) U.S. Cl.
CPC ............ *B65B 29/10* (2013.01); *B65D 81/3222* (2013.01); *B65B 2220/14* (2013.01); *B65B 2230/02* (2013.01); *B65D 35/42* (2013.01)

(58) Field of Classification Search
CPC .. B65D 81/3222; B65D 83/682; B65D 35/42; B65D 81/3266; B65D 81/3211; B65D 1/04; B65D 21/0231; B65D 2577/043; B65F 1/1623; B65F 1/08; A47G 19/2283; A47G 19/26; B05B 11/3084; B05C 17/00553; A47J 36/06
USPC .......... 222/135, 129, 137, 136; 206/219, 222; 215/6, 10; 220/812, 811, 810, 23.89, 220/23.88, 23.86, 23.83
See application file for complete search history.

(56) References Cited

U.S. PATENT DOCUMENTS 3,156,369 A * 11/1964 Bowes et al. ................. 206/222
3,220,588 A * 11/1965 Lipari ........................... 206/222
4,183,959 A    1/1980 Wood et al.
5,064,121 A * 11/1991 Bolduc ......................... 239/309
5,246,142 A *  9/1993 DiPalma et al. .............. 222/129
5,992,693 A * 11/1999 Albisetti ...................... 222/129

(Continued)

FOREIGN PATENT DOCUMENTS

GB        2417231        2/2006

OTHER PUBLICATIONS

Capsule-pharmacy definition, Wikipedia, the free encyclopedia, downloaded on Mar. 12, 2012 from http://en.wikipedia.org/wiki/Capsule_(pharmacy), 4 pages.

(Continued)

*Primary Examiner* — Kevin P Shaver
*Assistant Examiner* — Stephanie E Williams
(74) *Attorney, Agent, or Firm* — Dentons US LLP

(57) ABSTRACT

The present invention relates to a two compartment container, and more particularly, to a two compartment container for holding two fluids separate until such time as mixing is desired. A first compartment holds a first fluid. A second compartment holds a second fluid. A door separates the first compartment and the second compartment. A shaft holds the door in a closed position when the shaft is in a first position. A release component, coupled to the shaft, moves the shaft to a second position causing or allowing the door to move to an open position. The first fluid and the second fluid mix in response to the door moving to the open position.

20 Claims, 18 Drawing Sheets

(56) References Cited

U.S. PATENT DOCUMENTS

| | | | | |
|---|---|---|---|---|
| 6,003,728 | A * | 12/1999 | Elliott | 222/81 |
| 6,513,650 | B2 * | 2/2003 | Mollstam et al. | 206/222 |
| 6,572,892 | B1 | 6/2003 | Ioulalen et al. | |
| 7,025,200 | B2 * | 4/2006 | Fontana | 206/222 |
| 7,622,132 | B2 | 11/2009 | Lee et al. | |
| 7,854,104 | B2 * | 12/2010 | Cronin et al. | 53/420 |
| 7,870,952 | B2 * | 1/2011 | Fontana | 206/222 |
| 7,874,420 | B2 * | 1/2011 | Coon | 206/219 |
| 2002/0020636 | A1 * | 2/2002 | Bergamini et al. | 206/219 |
| 2002/0179461 | A1 * | 12/2002 | Mollstam et al. | 206/222 |
| 2005/0174881 | A1 * | 8/2005 | Ki | 366/130 |
| 2006/0151414 | A1 * | 7/2006 | Mullen | 215/227 |
| 2008/0089913 | A1 | 4/2008 | Kallmayer et al. | |
| 2008/0093326 | A1 * | 4/2008 | Cho | 215/228 |
| 2009/0155354 | A1 | 6/2009 | McLean et al. | |
| 2009/0260999 | A1 * | 10/2009 | Yang et al. | 206/219 |

OTHER PUBLICATIONS

Jinnapat et al., The manufacture of spherical salt beads and their use as dissolvable templates for the production of cellular solids via a powder metallurgy route, Journal of Alloys and Compounds, 2010, pp. 43-47, vol. 499, No. 1.

Kofuji et al., The Controlled Release of a Drug from Biodegradable Chitosan Gel Beads, Chem. Pharm. Bull., 2000, pp. 579-581, vol. 48, No. 4.

Naguib, Soft Gel Capsules: An Elegant & Versatile Dosage Form, Supplement Industry Executive, downloaded on Mar. 12, 2012 from http://www.hnherbs.com/SoftGel.pdf, 6 pages.

Narkar et al., Stomach-Specific Controlled Release Gellan Beads of Acid-Soluble Drug Prepared by Ionotropic Gelation Method, AAPS PharmSciTech, 2010, pp. 267-277, vol. 11, No. 1.

International Search Report and Written Opinion corresponding to PCT/US2013/033155 dated Jul. 25, 2013.

* cited by examiner

16

4

CONVERTIBLE TWO COMPARTMENT CONTAINER

TECHNICAL FIELD

The present invention relates to a convertible two compartment container, and more particularly, to a convertible two compartment container that holds two fluids separate, and converts into a one compartment container to mix the two fluids.

BACKGROUND OF THE INVENTION

Typically, containers having two compartments include independent vessels or storage compartments that can hold various combinations of fluids, powders, or pastes that are stored in a separated state until the user of a container decides to mix and utilize the products. These types of containers are most useful where keeping product ingredients separate until use extends shelf life or enhances product effectiveness, in contrast to containers where a product is premixed prior to shipping. Applications for such containers include, storage of cosmetic creams and lotions, skin cleaners, shampoos, conditioners and hair coloring. While many containers having two compartment containers exist, many contain complicated stopper configurations such as U.S. Pat. No. 5,692,644 while some require the user to connect the two containers prior to mixing, see for example U.S. Pat. No. 6,910,573.

Many existing containers with two compartments require the user to screw mechanisms together, as described by U.S. Pat. No. 6,126,032, or to use a driving force to cause the mechanisms to mix, as described by U.S. Pat. No. 5,692,644. As a result, the user must exert a significant force to cause mixing to occur.

Furthermore, existing containers with two compartments are not constructed to elicit responses from users based on their impressions or feelings experienced during the mixing of ingredients. Oftentimes, the user also cannot view the mixing of the ingredients.

SUMMARY

The present invention relates to a convertible two-compartment container. A first compartment holds a first fluid. A second compartment holds a second fluid. A door separates the first compartment and the second compartment. A shaft holds the door in a closed position when the shaft is in a first position. A release component, coupled to the shaft, moves the shaft to a second position causing or allowing the door to move to an open position. The first fluid and the second fluid mix in response to the door moving to the open position.

In an embodiment, the first compartment is a windowed compartment.

In an embodiment, the door comprises a plurality of door serrations for mating with a plurality of shaft serrations of the shaft to hold the door in the closed position when the shaft is in the first position. In an embodiment, the plurality of shaft serrations move out of contact with the door serrations when the shaft moves to the second position.

In an embodiment, the door is nontransparent to hide the second compartment holding the second fluid from view.

In an embodiment, the shaft is coupled to the second compartment.

In an embodiment, the shaft moves from the first position to the second position by moving in a downward direction.

In an embodiment, the release component comprises a button and a spring coupled to the button. The spring contacts the shaft when the button is activated, causing or allowing the door to move to the open position.

In an embodiment, the first fluid comprises beads or capsules each capsule including a coating, such as a degradable coating and the second fluid comprises an acid reactive to the degradable coating of the capsules of the first fluid when the first fluid and the second fluid are mixed.

The present invention further relates to a method for preparing a container. A first fluid is inserted in a first compartment. A second fluid is inserted in a second compartment. The first compartment and the second compartment are separated with a door. A shaft is positioned to hold the door in a closed position when the shaft is in a first position. A release component is coupled to the shaft, wherein activation of the release component causes the shaft to move to a second position which causes or allows the door to move to an open position facilitating mixture of the first fluid and the second fluid.

In an embodiment, the release component is activated causing the first fluid and the second fluid to mix.

In an embodiment, positioning the shaft to hold the door in a closed position when the shaft is in the first position comprises positioning a plurality of shaft serrations of the shaft to mate with a plurality of door serrations of the door to hold the door in the closed position when the shaft is in the first position. The plurality of shaft serrations move out of contact with the door serrations when the shaft moves to the second position.

In an embodiment, coupling a release component to the shaft comprises coupling a spring to the shaft and coupling a button to the spring. Activating the button causes or allows the door to move to the open position.

In an embodiment, the first compartment is a windowed compartment.

In an embodiment, the door is nontransparent to hide the second compartment holding the second fluid from view.

In an embodiment, the shaft is coupled to the second compartment.

In an embodiment, the shaft moves from the first position to the second position by moving in a downward motion.

The present invention further relates to a bead or capsule comprising a coating and a non-solid or a substantially non-solid substance, wherein (a) the substance is suitable for dermatological application and (b) the coating (i) is at least substantially impervious to the substance under ambient conditions when separated from an aqueous acidic solution and (ii) is degraded, substantially degraded, or becomes liquid permeable when contacted with an acidic aqueous solution.

BRIEF DESCRIPTION OF THE DRAWINGS

The present disclosure, in accordance with one or more embodiments, is described in detail with reference to the following figures. The drawings are provided for purposes of illustration only and merely depict typical or example embodiments. These drawings are provided to facilitate the reader's understanding of the apparatus and methods and shall not be considered limiting of the breadth, scope, or applicability of the invention. It should be noted that for clarity and ease of illustration these drawings are not necessarily made to scale.

Some of the figures included herein illustrate various embodiments from different viewing angles. Although the accompanying descriptive text may refer to such views as "top," "bottom" or "side" views, such references are merely descriptive and do not imply or require that all embodiments

The figures are not intended to be exhaustive or to limit the embodiments to the precise form disclosed. It should be understood that the various embodiment can be practiced with modification and alteration, and that the invention is limited only by the claims and the equivalents thereof.

DETAILED DESCRIPTION

The embodiments described herein are exemplary. Descriptions in terms of these embodiments is provided to allow various features to be portrayed in the context of an exemplary application. As will be clear to one of ordinary skill in the art, the invention can be implemented in different and alternative embodiments without departing from the spirit or scope of the invention.

Unless defined otherwise, all terms used herein have the same meaning as is commonly understood by one of ordinary skill in the art to which this invention belongs.

Figure 1:
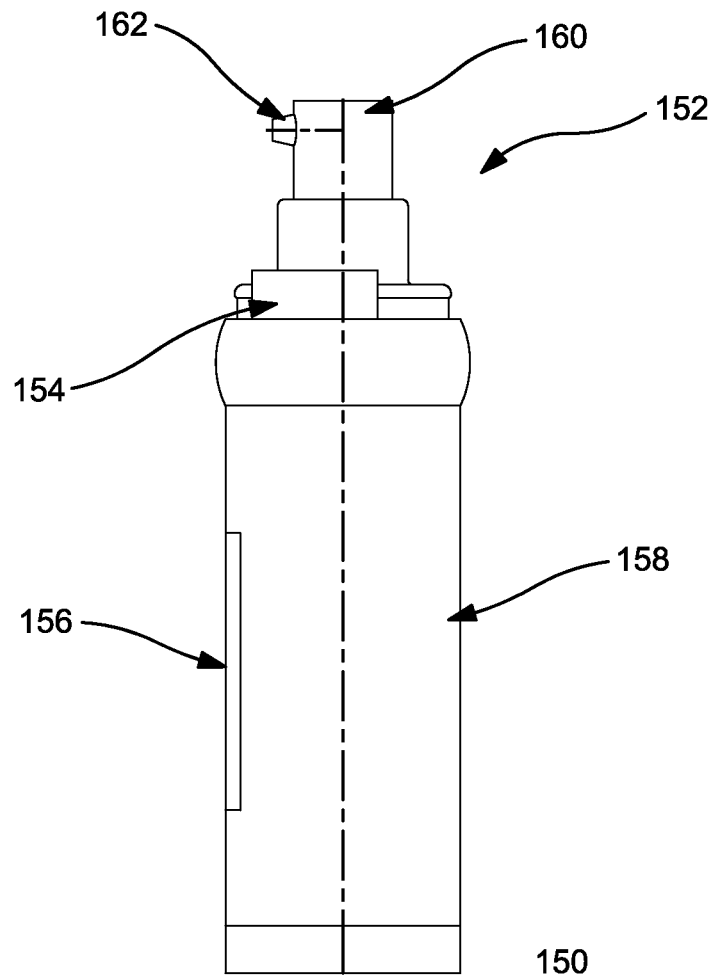
FIG. 1 is a side exterior view of a convertible two-compartment container in accordance with an exemplary embodiment.

FIG. 1 depicts a side exterior view of a convertible two-compartment container in accordance with an exemplary embodiment. Two-compartment container 150 includes a pumping mechanism 152, a button 154, a window 156, and compartment container 158. Pumping mechanism 152 facilitates dispensing of a fluid or fluids contained within two-compartment container 150. When a pump button 160 is depressed, a fluid or fluid from within compartment container 158 is dispensed through spout 162. Compartment container 158 may include two compartments (not shown) within, one of which is viewable through window 156. Each of the two compartments holds a different fluid. Button 154, when depressed, causes the two compartments within compartment container 158 to convert to become a single container, causing the different fluids held by the two compartments to mix. The mixing process is viewable through window 156.

Figure 2:
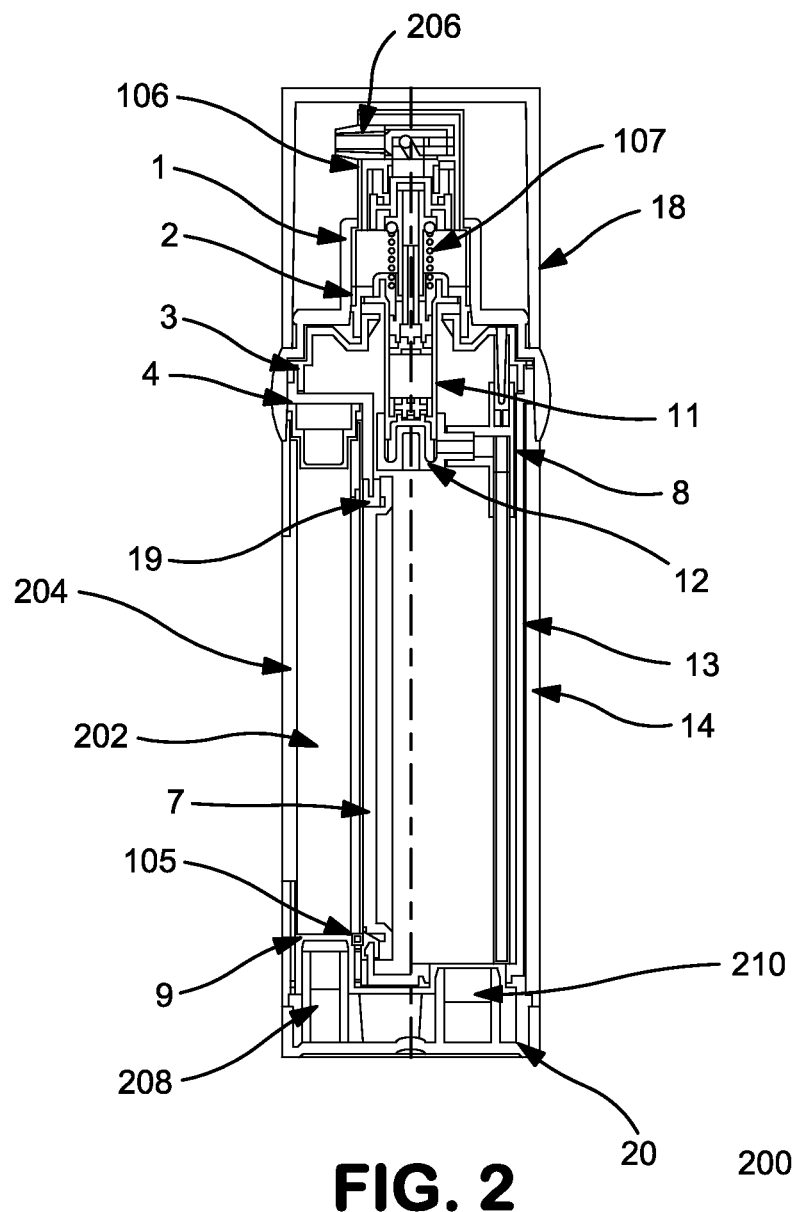
FIG. 2 is a cross sectional view of a convertible two-compartment container in accordance with an exemplary embodiment.

FIG. 2 depicts a cross sectional view of a convertible two-compartment container in accordance with an exemplary embodiment. Two compartment container 200 includes shoulder 1, pump inner cap 2, adapter 3, window cap 4, door 7, dip tube adapter 8, bottle packing element 9, pump housing 11, elbow 12, inner compartment 13, outer compartment 14, over cap 18, rubber insert 19, base 20, tight rubber 105, button assembly 106, and pump assembly 107. Also shown are a windowed compartment 202, including a window 204.

Shoulder 1 houses pump inner cap 2, which is coupled to shoulder 1. Also housed within shoulder 1 is pump assembly 107, which is coupled to pump inner cap 2. Pump housing 11 covers and acts as a protective translucent cover for pump assembly 107. A top portion of shoulder 1 includes an opening (not shown) which is configured to receive button assembly 106. Button assembly 106 couples with pump assembly 107 within shoulder 1. Pump assembly 107 is further coupled to adapter 4. Adapter 4 is coupled to dip tube adapter 8 via elbow 12. Dip tube adapter 8 may receive fluid from inner compartment 13 through a dip tube. When button assembly 106 is activated or depressed, fluid from inner compartment 13 is lifted through dip tube adapter 8, through adapter 4, and into pump assembly 107 for dispensing through spout 206. Over cap 18 may be placed atop shoulder 1 to cover button assembly 106 when two-compartment container 200 is not in use and to prevent accidental dispensing of fluids.

Door 7 separates inner compartment 13 from windowed compartment 202. A different fluid may be stored in each of inner compartment 13 and windowed compartment 202. Door 7 is held in a closed position by a shaft (not shown). When door 7 is opened, the fluids from inner compartment 13 and windowed compartment 202 may mix. When door 7 is in the closed position, when button assembly 106 is activated or depressed, only fluid from inner compartment 13 may be dispensed through spout 206. When door 7 is opened or moves to an open position, activation or depression of button assembly 106 causes a mixture of the fluids from inner compartment 13 and windowed compartment 202 to be dispensed through spout 206. Mixture of the fluids from inner compartment 13 and windowed compartment 202 takes place because when door 7 opens, an opening between inner compartment 13 and windowed compartment 202 allows the fluids to mix. Rubber insert 19 may be placed around the hole to cushion door 7.

Bottle packing element 9 is a component that is used to hold together or attach inner compartment 103 and windowed compartment 5. Bottle packing element 9 includes two cylindrical plugs 208 and 210. Cylindrical plug 208 mates with a cylindrical hold on an underside of windowed compartment 202. Cylindrical plug 210 mates with a cylindrical hole on an underside of inner compartment 13. When bottle packing element 9 is mated with and attached to both inner compartment 103 and windowed compartment 202, inner compartment 103 and windowed compartment 202 are held in place within outer compartment 14. Bottle packing element 9 also acts to prevent any mixture of inner compartment and windowed compartment 202 before door 7 is opened.

Outer compartment 14 which is positioned beneath and coupled to shoulder 1 includes windowed compartment 202 and inner compartment 13. Outer compartment 14 also houses dip tube adapter 8 and elbow 12. Windowed compartment 202 is included within outer compartment 14. Windowed compartment 202 includes a window 204 which allows for viewing of any fluid stored within windowed compartment 202 when door 7 is closed. Window 204 also allows for viewing of a mixture of fluids contained in windowed compartment 202 and inner compartment 13 when door 7 is open.

The contents or fluids stored within inner compartment 13 are not visible to a user of two-compartment container because door 7 separates inner compartment 13, and window 204 only facilitates viewing of the contents or fluids stored within windowed compartment 202. As discussed above, a dip tube coupled to dip tube adapter 8 extends into inner compartment 13 so that fluids from inner compartment 13 may be dispensed. Fluids stored in windowed compartment 202 may not be separately dispensed. When fluids from windowed compartment 202 and inner compartment 13 are mixed, the mixture of fluids may be dispensed through the dip tube coupled to dip tube adapter via inner compartment 13. When door 7 is opened, windowed compartment 202 and inner compartment 13 are essentially combined as one compartment. Thus, container 200, which includes inner compartment 13 and windowed compartment 202, is a convertible two-compartment container that converts from two compartments (windowed compartment 202 and inner compartment 13) into a single compartment comprising both windowed compartment 202 and inner compartment 13 when door 7 is opened.

Two-compartment container 200 also includes a button, which is not shown in FIG. 2, but functions similarly to button 104 described above with regard to FIG. 1 More specifically, when this button is activated or depressed, door 7 is released, thus facilitating mixture of fluids from inner compartment 13 and windowed compartment 202. Further description of the button is provided below.

While inner compartment 13 and windowed compartment 202 may store fluids, wherein fluids include liquids, gases, and plasmas, solids may also be stored within inner compartment 13 and windowed compartment 202.

The present disclosure additionally relates, at least in part, to a coated non-solid or a substantially non-solid substance. The coated non-solid or a substantially non-solid substance can be in partially spherical form, substantially spherical form, or spherical form. For example, the substance can be in the form of a bead. As another example, the substance can be in the form of a capsule. The balance of the discussion will refer to the encapsulated substance as a bead or capsule but one of ordinary skill will understand that such term includes any shape suitable for the functions described herein.

The substance encapsulated in the capsule or bead can be a non-solid substance, such as liquid or semi-liquid (e.g., a gel). The substance can be suitable for dermatological application. The substance can include, for example, a dissolved solution, suspension or dispersion of solid particles within a non-solid substance. The substance can be encapsulated in a coating, as described herein. Dissolution of the substance can be enhanced by an additive, such as polyethylene glycols (PEG), cyclodextrins, carboxymethylcellulose or emulsifiers.

The non-solid or substantially non-solid substance(s) can be partially covered, coated, or encapsulated by a coating; substantially covered, coated, or encapsulated by a coating; or covered, coated, or encapsulated by a coating. The coating can be a degradable coating. For example, the coating can be a degradable membrane. A degradable coating can be of a material that will melt, dissolve, disintegrate or dissipate to partially release, substantially release, or release the non-solid or substantially non-solid substance(s) when in contact with an acidic solution. For example, the coating can degrade when placed in contact with a solution comprising an acid. As another example, the non-solid or substantially non-solid substance(s) can be enclosed in a membrane coating which will melt, dissolve, disintegrate or dissipate to release the substance when placed in contact to the solution comprising an acid.

The coating can be any solid or semi-solid material (e.g., a film) that is impervious to the encased liquid, is stable, and has a long shelf-life in a storage environment. The coating can retain integrity while being stored. The coating can include various shapes, sizes, thicknesses, melting temperatures or chemical compositions to accommodate needs of the substance to be delivered into the solution, as described herein. Various thicknesses, melting temperatures, or chemical compositions of the membrane can be according to the solution that is introduced to the capsules or beads. The coating can also contain an active ingredient that may also be contained within the liquid or semi-liquid filled bead or capsule. A capsule or bead according to the invention may be manufactured in accordance with known encapsulation techniques.

The coating can include a thin film of membrane material. A coating can include, for example, polyvinyl alcohol, polyethylene oxide, hydrogel, soft-gel, collagen, or gelatin. A coating can be produced with contents that will react to the pH of the liquid in inner compartment 13. A coating can optionally contain a basic substance to enhance membrane solubility in the acidic solution. A coating can be formed of a polymer (e.g., a synthetic polymer or a natural polymer) that is pharmacologically acceptable. Examples of polymeric materials include polyanhydrides, polyorthoesters, polyglycolic acid, polylactic acid, polyethylene vinyl acetate, and copolymers and combinations thereof. A coating can include one or more material selected from polylactic acid (PLA), polyglycolid acid (PGA), copolymers of lactic acid and glycolic acid (PLGA), polycaprolactone, polyphosphoester, polyorthoester, poly(hydroxy butyrate), poly(diaxanone), poly(hydroxy valerate), poly(hydroxy butyrate-co-valerate), poly(glycolide-co-trimethylene carbonate), polyanhydrides, polyphosphoester, poly(ester-amide), polyphosphoeser, polyphosphazene, poly(phosphoester-urethane), poly(amino acids), polycyanoacrylates, biopolymeric molecules such as fibrin, fibrinogen, cellulose, starch, collagen and hyaluronic acid, and mixtures and copolymers of the foregoing. A coating can include a natural polymer, such as collagen, gelatin, fibrin, or chitin. A coating can include a synthetic polymer, such as poly(dl-ε-caprolactone), poly(lactic-coglycolic) acid (PLGA), poly(D,L-lactide) (PLA), poly-L-lactic acid (PLLA), a polyanhydride, or chitosan. For example, a coating can be formed of a polymer, such as a polyalkylene oxide (e.g., polyethylene oxide). A coating can include a soft-gel, where the soft gel can include, for example, an animal collagen or plant based materials (e.g., Irish Moss). For example, a coating can include a hydrogel, such as chitosan.

In some embodiments, upon contact of the capsule or bead and the acidic liquid, the liquid or semi-liquid in the capsule or bead will be expelled as the coating degrades in the aqueous solution. A number of release mechanisms facilitating the release of the coated liquid or semi-liquid substance from the capsule or bead are possible. Release of the substance can be activated by a variety of mechanisms. Release mechanisms include, but are not limited to, temperature, solubility, pH, oxidation, mechanical deformation, osmotic potential, a "weak spot" or imperfection on the capsule or bead, an enzymatic trigger, or a combination thereof. The release of the liquid or semi-liquid substance can be based on the solubility of the coating material under acidic aqueous conditions. pH activated release mechanisms can, for example, include use of an enteric type coating. Enteric coatings, such as those for targeted drug release in oral delivery, are well known and can be adapted for use as a coating in accord with the description herein. In some embodiments, the coating includes a film that is insoluble at neutral pH and soluble when conditions become acidic. Other pH-activated release mechanisms which can be employed include deflocculation of a polymer latex shell or oxidation activated mechanisms. In some embodiments, the coating is stable across an ambient temperature range but can melt, dissolve, or dissipate in response to pH level so as to release the liquid or semi-liquid substance.

In an embodiment, windowed compartment 202 holds a plurality of liquid or semi-liquid (e.g., a gel) filled capsules or beads, each capsule including a coating, such as a degradable coating. Inner compartment 13 may hold a liquid comprising an acid reactive to the degradable coating of the capsules. When door 7 is opened, allowing contact of the liquid or semi-liquid filled capsules or beads and the liquid comprising an acid, the acidic solution can react with the degradable coating of the capsules, causing the degradable coating to break down to facilitate release of the liquid or semi-liquid from the capsules or beads. In another embodiment, the liquid filled capsules can comprise a coating with a plurality of holes on its exterior surface. The plurality of holes can receive the liquid comprising an acid from inner compartment 13, which permeates the coating, facilitating break down of the coating and release of the liquid or semi-liquid from the capsules or beads. In another embodiment, the coating may include polymers reactive to the acid of the liquid from inner compartment 13.

In an embodiment, the bead or capsule comprises a coating and a non-solid or a substantially non-solid substance, wherein (a) the substance is suitable for dermatological application and (b) the coating (i) is at least substantially impervious to the substance under ambient conditions when separated from an aqueous acidic solution and (ii) is degraded, substantially degraded, or becomes liquid permeable when contacted with an acidic aqueous solution.

Figure 3:
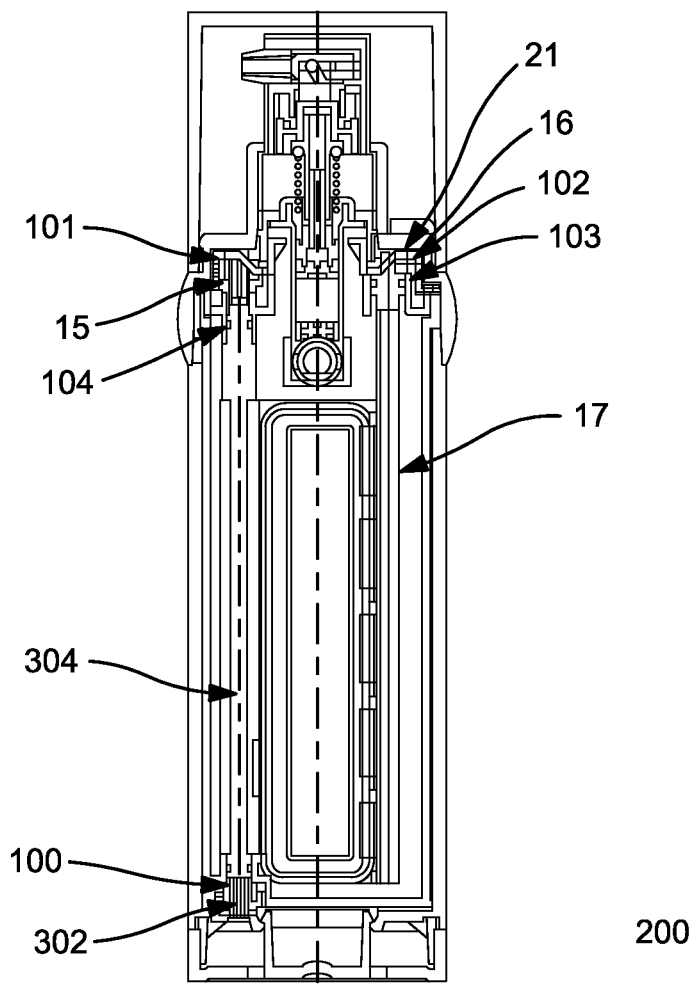
FIG. 3 is a cross sectional view of a convertible two-compartment container in accordance with an exemplary embodiment.

FIG. 3 depicts another, different cross sectional view of a convertible two-compartment container in accordance with an exemplary embodiment. Two-compartment container 200, as shown by FIG. 3, includes door hinge adapters 15 and 302, button 16, button shaft 17, door hinge springs 100 and 101, spring 102, button O-ring 103, and door hinge O-ring 104.

Door hinge adapters 15 and 302 are coupled to door hinge springs 101 and 100, respectively. Door hinge springs 100 and 101 are coupled to door shaft 304 of door 7. In an embodiment, door hinge springs 100 and 101 are not necessary, and thus are not coupled to door shaft 304 of door 7. Button 16 is in turn coupled to button shaft 17 via spring 102. Button 16 is coupled to a spring 102 that compresses when button housing 21 is activated or depressed. Spring 102 is coupled to button shaft 17. A force received from a user by button 16 causes spring 102 to compress, and change a position of button shaft 17. Button shaft 17 includes a plurality of shaft serrations that are configured to mate with a plurality of door serrations of door 7.

When the shaft serrations and door serrations are mated, door 7 is held in a closed position. Thus, when button shaft 17 is in a first position, door 7 is in a closed position. When button 16 is activated or depressed, the force received by button 16 causes spring 102 to compress and change the position of button shaft 17 from a first position to a second position where the shaft serrations and door serrations are no longer mated and in contact. In an embodiment, button shaft 17 moves from a first position to a second position by moving downwards or in the same direction as the force applied to button 16 by a user.

As button shaft 17 moves from a first position to a second position, the shaft serrations separate from the door serrations of door 7. As this occurs, door hinge springs 100 and 101 cause door 7 to open. When door 7 is in a closed position, door hinge springs 100 and 101 are in a compressed state. As door 7 opens, door hinge springs 100 and 101 uncompress, forcing door 7 to swing open. When door 7 is opened, windowed compartment 202 and inner compartment 13 are converted into a single container. Fluids from windowed compartment 202 and inner compartment 13 are allowed to mix. A user may watch the mixture occur through window 202 of windowed compartment 202.

In an embodiment where door hinge springs 100 and 101 are not necessary, a center door spring (not shown) may be used to hold door 7 in a closed position. In this embodiment, when button shaft 17 moves from a first position to a second serration, the center door spring uncompresses from a compressed state to allow door 7 to open. Further explanation of this embodiment is provided with respect to FIG. 8B below.

Figure 4:
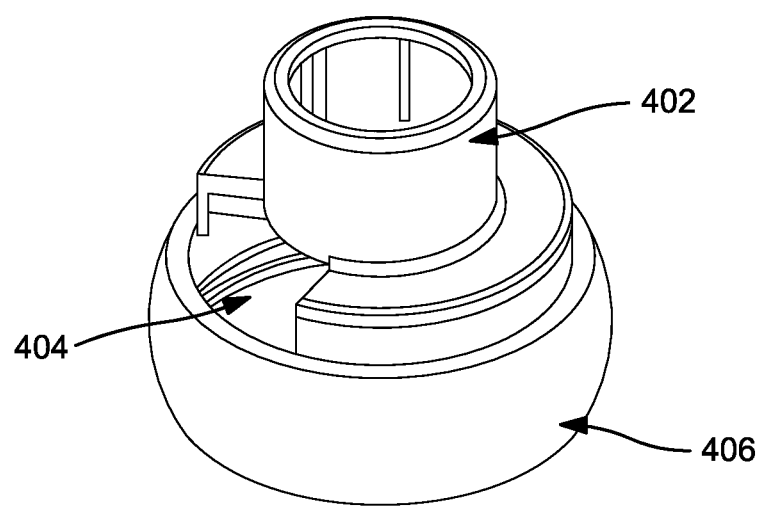
FIG. 4 is a perspective view of a container shoulder of a convertible two-compartment container in accordance with an exemplary embodiment.

FIG. 4 depicts a perspective view of a container shoulder of a convertible two-compartment container in accordance with an exemplary embodiment. FIG. 4 is a perspective view of shoulder 1. Shoulder 1 includes a top conduit 402 for receiving or mating with button assembly 106. Button assembly 106 is received by top conduit 402 from a top end. A lower end of top conduit 402 couples with pump inner cap 2. Pump inner cap 2 secures the connection between button assembly 106 and pump assembly 107.

Shoulder 1 also includes a button receiving opening 404. Button receiving opening 404 is configured to receive button 16 that interacts with button shaft 17 causing or allowing door 7 to open. Shoulder 1 additionally includes a bottom conduit 406. Bottom conduit 406 houses adapter 3 which is coupled to pump assembly 107.

Figure 5:
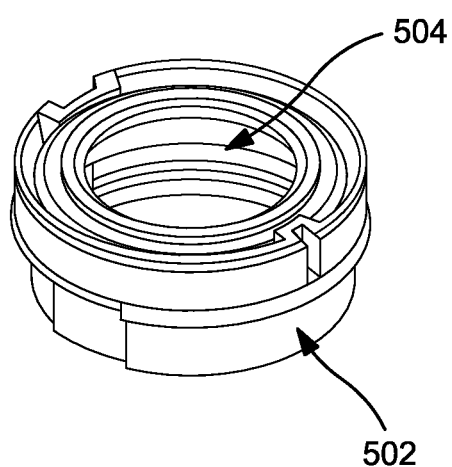
FIG. 5 is a perspective view of a pump inner cap of a convertible two-compartment container in accordance with an exemplary embodiment.

FIG. 5 depicts a perspective view of a pump inner cap of a convertible two-compartment container in accordance with an exemplary embodiment. FIG. 5 shows a perspective view of pump inner cap 2. Pump inner cap 2 includes a grooved base 502 for coupling with corresponding grooves within shoulder 1. Pump inner cap 2 also includes an opening 504 for receiving and coupling with button assembly 106.

Figure 6:
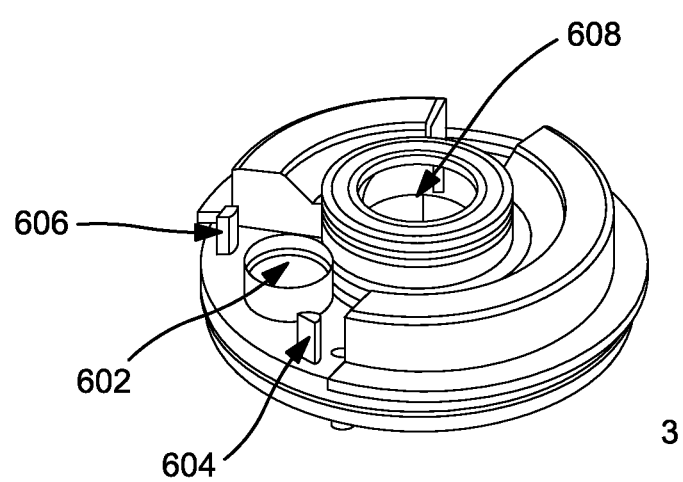
FIG. 6 is a perspective view of an adapter of a convertible two-compartment container in accordance with an exemplary embodiment.

FIG. 6 depicts a perspective view of an adapter of a convertible two-compartment container in accordance with an exemplary embodiment. FIG. 6 shows adapter 3, which is designed to couple with an interior of bottom conduit 406 of shoulder 1. Adapter 3 further includes a first opening 602 for receiving button shaft 17. Top end 1004 of button shaft 17 is held by first opening 602. Top end 1004 of button shaft 17 may be inserted upwards through first opening 602. The top end 1004 of button shaft 17 may be coupled to spring 102 (not shown). Spring 102 may comprise a two spring configuration, each spring configured for attachment with attachment units 604 and 606, respectively. Adapter 3 additionally includes a second opening 608 configured to receive a lower end of pump assembly 107.

Figure 7:
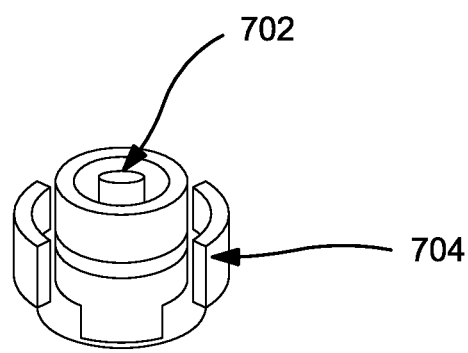
FIG. 7 is a perspective view of a hinge adapter of a convertible two-compartment container in accordance with an exemplary embodiment.

FIG. 7 depicts a perspective view of a hinge adapter of a convertible two-compartment container in accordance with an exemplary embodiment. FIG. 7 depicts an exemplary door hinge adapter 15. Door hinge adapter 302, also described above, may have the same design and functionality of door hinge adapter 15. Door hinge adapter 15 may be coupled to a top end or bottom end of door hinge 304 of door 7. Door hinge adapter 15 includes a hinge opening 702 which may mate with either the top end or the bottom end of door hinge 304. Door hinge adapter 15 further includes a door spring gap 704 which supports door hinge spring 100 or 101.

Figure 8A:
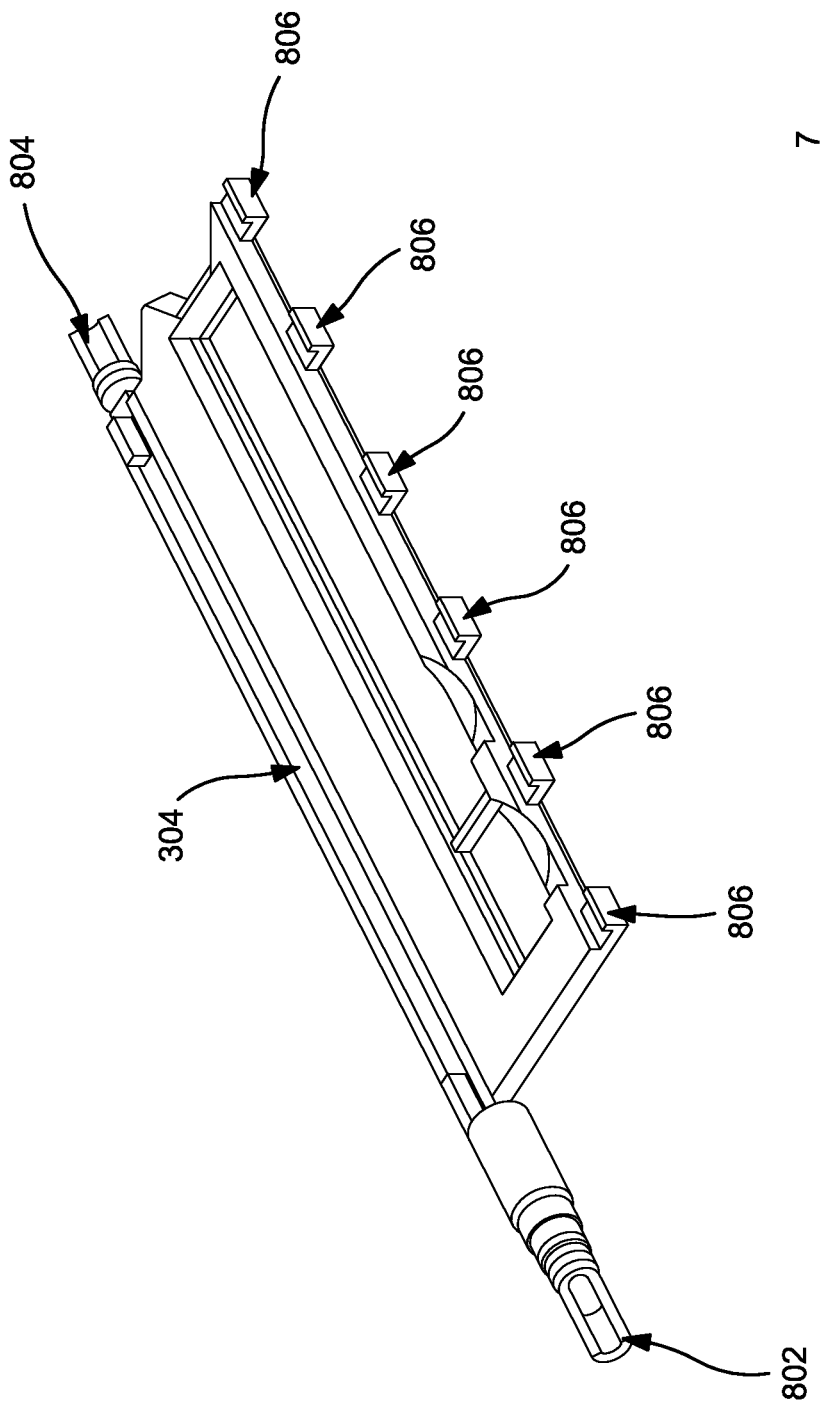
FIG. 8A is a perspective view of a door separating a first compartment and a second compartment of a convertible two-compartment container in accordance with an exemplary embodiment.

FIG. 8A depicts a perspective view of a door for separating a first compartment and a second compartment of a convertible two-compartment container in accordance with an exemplary embodiment. FIG. 8A shows door 7, which is used to separate windowed compartment 202 and inner compartment 13, and more specifically, to keep fluids stored in each of windowed compartment 202 and inner compartment 13 from mixing until door 7 is opened. Door 7 includes door hinge 304, which itself includes a top door hinge end 802 and bottom door hinge end 804. Each of top door hinge end 802 and bottom door hinge end 804 supports door hinge spring 100 and door hinge spring 101, respectively, which are coiled around each of top door hinge end 802 and bottom door hinge end 804. Top door hinge end 802 additionally couples to door hinge adapter 15 and bottom door hinge end 804 couples to door hinge adapter 302. Door hinge spring 100 and door hinge spring 101 are both held in a compressed state when door 7 is closed.

Door 7 additionally includes a plurality of door serrations 806, which are configured to mate with shaft serrations of button shaft 17. When the plurality of door serrations 806 are mated with shaft serrations of button shaft 17, door 7 is held in a closed position. When door 7 is opened, the shaft serrations of button shaft 17 move apart from the plurality of door serrations 806. As this occurs, door hinge spring 100 and door hinge spring 101 uncompress and move to an uncompressed state, forcing door 7 to swing open facilitating mixture of fluids between windowed compartment 202 and inner compartment 13.

Figure 8B:
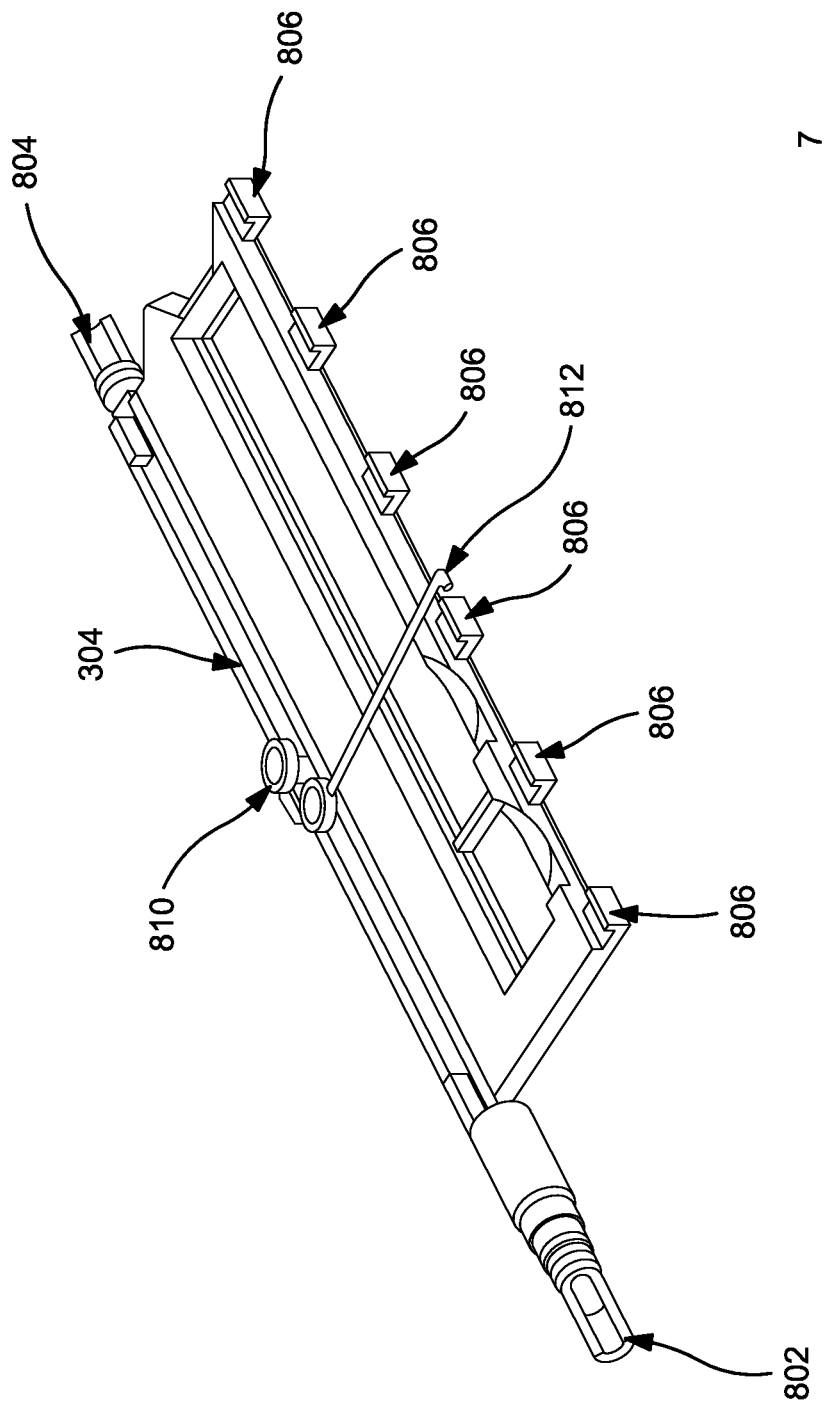
FIG. 8B is a perspective view of a door separating a first compartment and a second compartment of a convertible two-compartment container in accordance with an exemplary embodiment.

FIG. 8B depicts a perspective view of a door for separating a first compartment and a second compartment of a convertible two-compartment container in accordance with an exemplary embodiment. FIG. 8B shows an alternate embodiment of door 7, which is used to separate windowed compartment 202 and inner compartment 13, and more specifically, to keep fluids stored in each of windowed compartment 202 and inner compartment 13 from mixing until door 7 is opened. Door 7 includes door hinge 304, which itself includes a top door hinge end 802 and bottom door hinge end 804. Each of top door hinge end 802 and bottom door hinge end 804 do not required door hinge springs to keep door 7 closed. Top door hinge end 802 additionally couples to door hinge adapter 15 and bottom door hinge end 804 couples to door hinge adapter 302. In contrast to FIG. 8A, center spring 810 coupled to door 7, latches to button shaft 17 at an end 812. End 812 holds door 7 closed and keeps center spring 810 in a compressed position until door 7 is caused to open.

Door 7 additionally includes a plurality of door serrations 806, which are configured to mate with shaft serrations of button shaft 17. When the plurality of door serrations 806 are mated with shaft serrations of button shaft 17, door 7 is held in a closed position. When door 7 is opened, the shaft serrations of button shaft 17 move apart from the plurality of door serrations 806. As this occurs, end 812 of center spring 810 unlatches from button shaft 17 and center spring 810 itself uncompresses and moves to an uncompressed state, forcing door 7 to swing open facilitating mixture of fluids between windowed compartment 202 and inner compartment 13.

Figure 9:
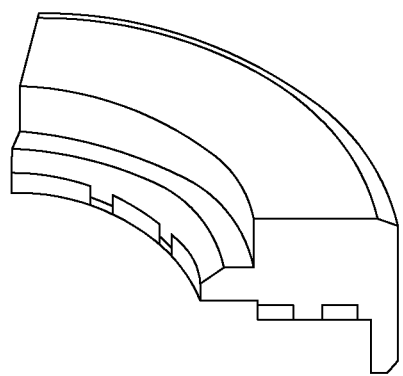
FIG. 9 is a perspective view of a button of a convertible two-compartment container in accordance with an exemplary embodiment.

FIG. 9 depicts a perspective view of a button of a convertible two-compartment container in accordance with an exemplary embodiment. FIG. 9 shows button 16 which is configured to fit in button receiving opening 404 of adapter 3. Button 16 houses spring 102 which couples with button shaft 17. When button 16 is activated or depressed by a user, spring 102 compresses, which causes button shaft 17 to move in a downwards motion. The plurality of shaft serrations of button shaft 17 separates from the plurality of door serrations 806, causing or allowing door 7 to open.

Figure 10:
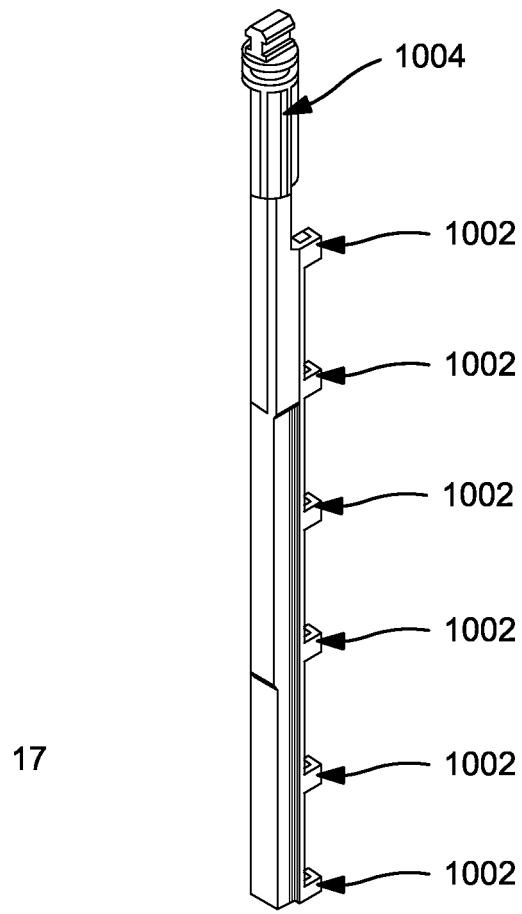
FIG. 10 is a perspective view of a shaft of a convertible two-compartment container in accordance with an exemplary embodiment.

FIG. 10 depicts a perspective view of a shaft of a convertible two-compartment container in accordance with an exemplary embodiment. FIG. 10 shows button shaft 17 including a plurality of shaft serrations 1002 and a top end 1004 which couples to spring 102 housed within button 16. When door 7 is in a closed position, shaft serrations 1002 are mated and connected to the plurality of door serrations 806 of door 7. Door 7 opens in response to a user activating or depressing button 16, which causes button shaft 17 to move in a downwards motion. The downward motion of button shaft 17 causes downward motion of the plurality of shaft serrations 1002, which disconnect from the plurality of door serrations 806.

Figure 11:
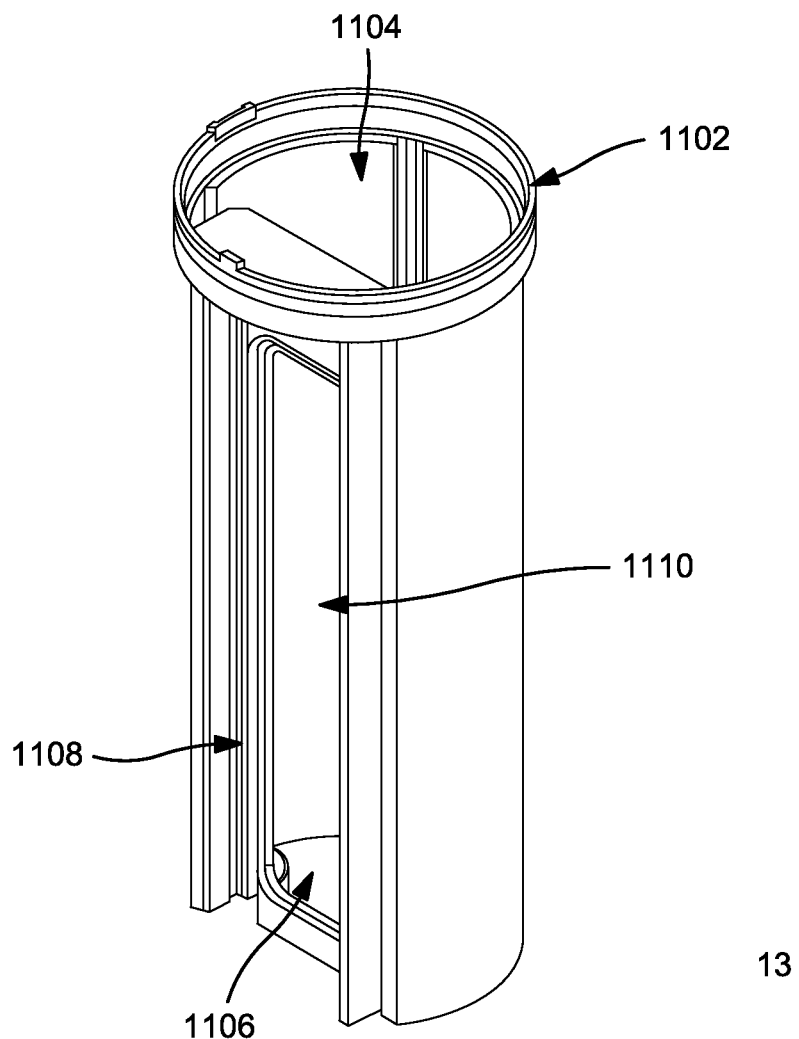
FIG. 11 is a perspective view of a compartment of a convertible two-compartment container in accordance with an exemplary embodiment.

FIG. 11 depicts a perspective view of a compartment of a convertible two-compartment container in accordance with an exemplary embodiment. FIG. 11 shows inner compartment 13. Inner compartment 13 couples to adapter 3 at a top end 1102. Inner compartment 13 includes a holding space 1104 for storing contents including fluids. A door opening 1106 of inner compartment 13 is typically covered by door 7 when door 7 is in a closed position. When door 7 opens, fluid from holding space 1104 of inner compartment 13 may freely flow through door opening 1106 and mix with fluid from windowed compartment 202. Inner compartment 13 further includes a dip tube opening 1108 that houses a dip tube coupled to dip tube adapter 8. The dip tube is used to transport fluid up through dip tube adapter 8 and into pump assembly 107 for dispensing. An opening 1110 of inner compartment 13 is configured to receive windowed compartment 202.

Figure 12:
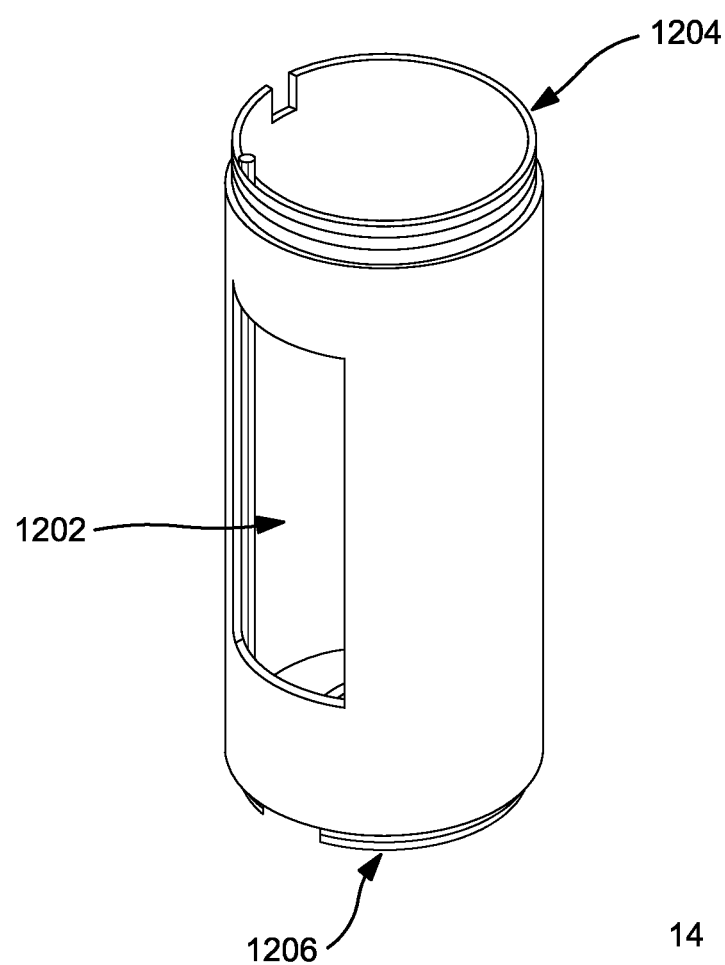
FIG. 12 is a perspective view of an outer container of a convertible two-compartment container in accordance with an exemplary embodiment.

FIG. 12 is a perspective view of an outer container of a convertible two-compartment container in accordance with an exemplary embodiment. FIG. 12 shows outer compartment 14. Outer compartment 14 is placed over inner compartment 13. Since outer compartment 14 completely covers inner compartment 13, the contents of inner compartment 13 may never be visible to a user of two-compartment container 200. Outer compartment 14 further includes a window hole 1202. Window hole 1202 supports a window 204 of windowed compartment 202. A windowed compartment 202 is placed within window opening 1110 of inner compartment 13, windowed compartment 202 is also enclosed within outer compartment 14. However, the contents of windowed compartment 202 may be visible through window 204 which is configured to fit within the space provided by window opening 1110. A top end 1204 of outer compartment 14 may be coupled to shoulder 1. A bottom end 1206 of outer compartment 14 may be coupled to base 20.

Figure 13:
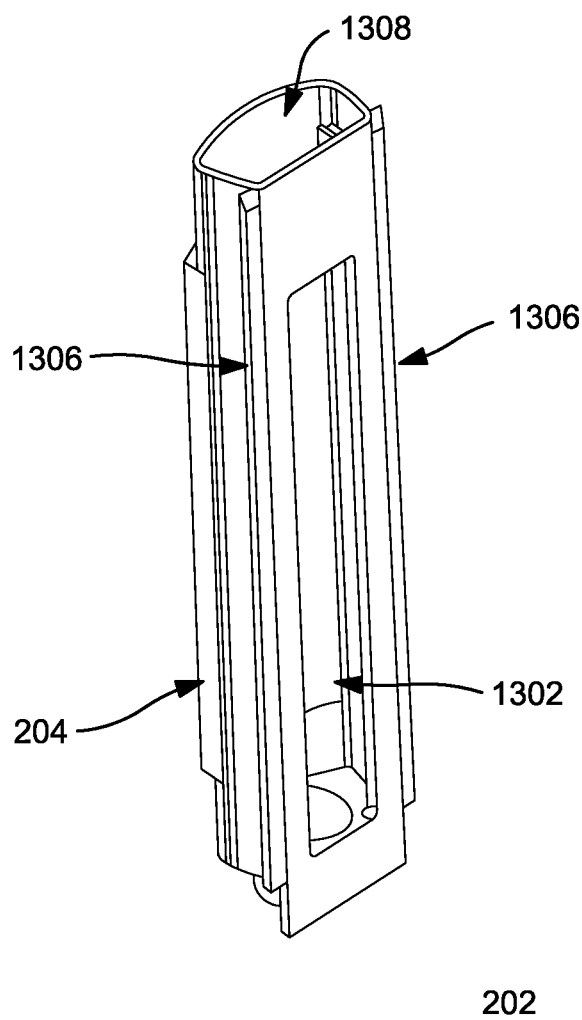
FIG. 13 is a perspective view of a windowed compartment of a convertible two-compartment container in accordance with an exemplary embodiment.

FIG. 13 depicts a perspective view of a window compartment of a convertible two-compartment container in accordance with an exemplary embodiment. FIG. 13 shows windowed compartment 202, which includes a door opening 1302, window 204, and rails 1306. Rails 1306 allow windowed compartment 202 to slidably attach with inner compartment 13 at window opening 1110 of inner compartment 13. Door opening 1302 is typically covered by door 7 when door 7 is in a closed position. When door 7 is in an open position, the contents or fluids from windowed compartment 202 may mix with contents or fluids from inner compartment 13. Window 204 advantageously allows users to view a fluid stored in windowed compartment 202, and the resulting process of the mixture of fluid in windowed compartment 202 with fluid from inner compartment 13. Windowed compartment 204 further includes window cap receiving opening 1308. Window cap receiving opening 1308 is configured to receive and mate with window cap 4, which further acts to prevent mixture of fluid between windowed compartment 204 and inner compartment 13 before door 7 opens.

Figure 14:
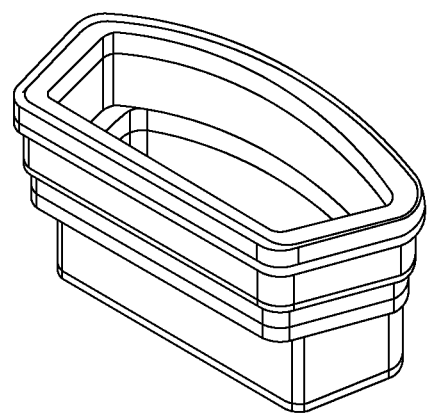
FIG. 14 is a perspective view of a cap of a convertible two-compartment container in accordance with an exemplary embodiment.

FIG. 14 depicts a perspective view of a cap of a convertible two-compartment container in accordance with an exemplary embodiment. FIG. 14 shows window cap 4, which may be inserted into a window cap receiving opening 1308 of windowed compartment 204 to serve as a plug, preventing mixture of fluid between windowed compartment 204 and inner compartment 13 before door 7 opens.

Figure 15:
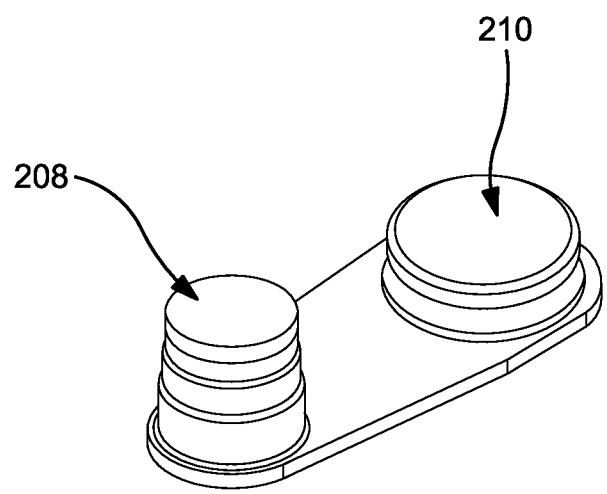
FIG. 15 is a perspective view of a packing element of a convertible two-compartment container in accordance with an exemplary embodiment.

FIG. 15 is a perspective view of a packing element of a convertible two-compartment container in accordance with an exemplary embodiment. FIG. 15 shows bottle packing element 9, which is used to ensure that bottom ends of both windowed compartment 204 and inner compartment 13 are sealed, thus also assisting to prevent mixture of fluid between windowed compartment 204 and inner compartment 13 before door 7 opens. Bottle packing element 9 includes cylindrical plugs 208 and 210. Cylindrical plug 208 mates with a cylindrical hold on an underside of windowed compartment 202. Cylindrical plug 210 mates with a cylindrical hole on an underside of inner compartment 13.

Figure 16:
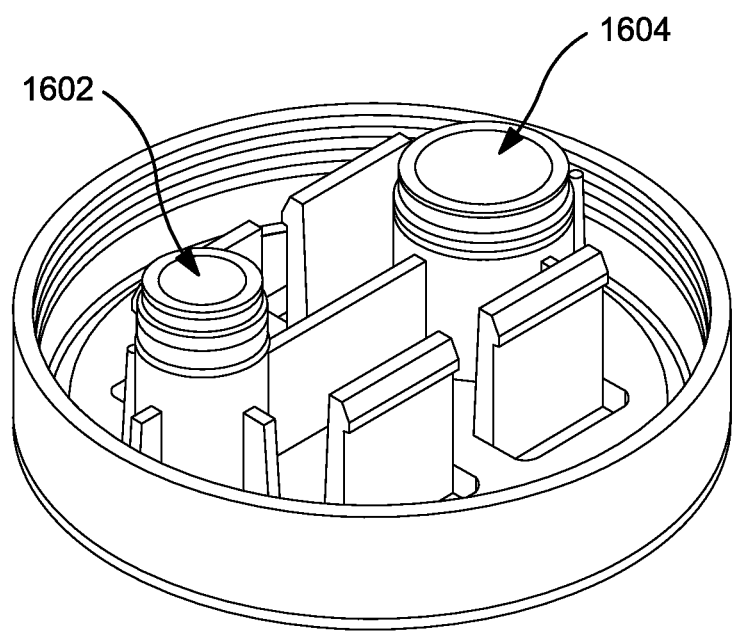
FIG. 16 is a perspective view of a base of a convertible two-compartment container in accordance with an exemplary embodiment.

FIG. 16 depicts a perspective view of a base of a convertible two-compartment container in accordance with an exemplary embodiment. Base 20 may be attached to bottom end 1206 of outer compartment 14. When attached, base plugs 1602 and 1604 mate with cylindrical plugs 208 and 210, respectively, of bottle packing element 9.

Figure 17:
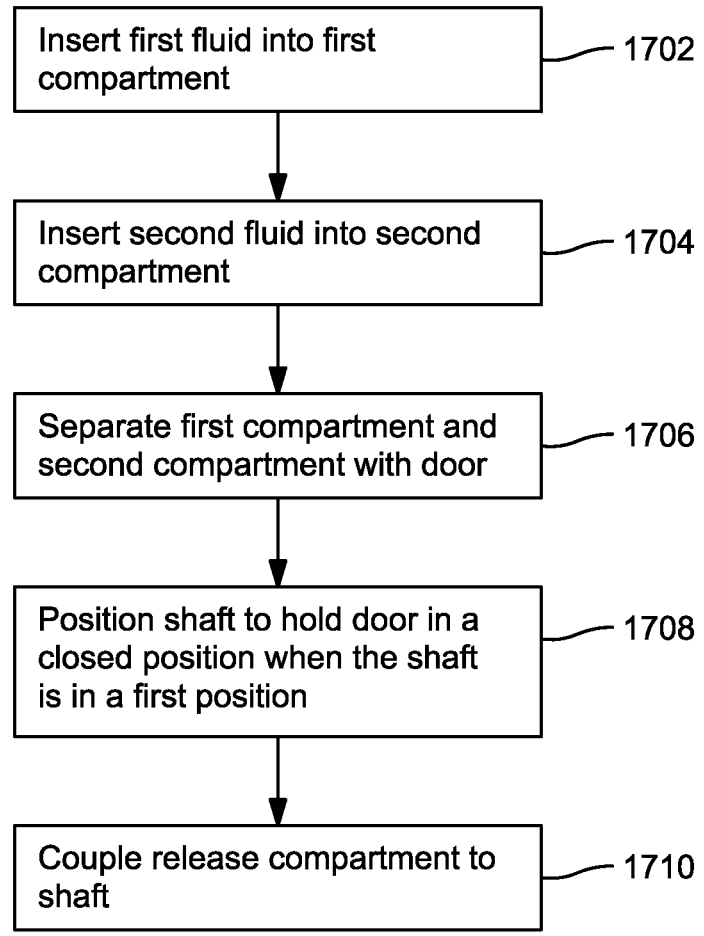
FIG. 17 is a flow chart showing steps for preparing a convertible two-compartment container in accordance with an exemplary embodiment.

FIG. 17 depicts a flow chart showing steps for preparing a convertible two-compartment container in accordance with an exemplary embodiment. At step 1702, a first fluid is inserted in a first compartment. For example, a first fluid is inserted into windowed compartment 202.

At step 1704, a second fluid is inserted in a second compartment. For example, a second fluid is inserted into inner compartment 13.

At step 1706, the first compartment and the second compartment are separated with a door. Door 7 may be installed between windowed compartment 202 and inner compartment 13 between door opening 1302 and door opening 1106. Door 7 may be nontransparent in order to hide inner compartment 13 from view through window 204 of windowed compartment 202.

At step 1708, a shaft is positioned to hold the door in a closed position when the shaft is in a first position. For example, button shaft 17 is positioned in a first position such that shaft serrations of button shaft 17 may mate with door serrations of door 7. Thus, the mating of the shaft serrations with the door serrations holds the door in the closed position. In an embodiment, a shaft, such as button shaft 17 may be coupled and integral with inner compartment 13.

At step 1710, a release component is coupled to the shaft. Activation of the release component causes the shaft to move to a second position which causes or allows the door to move to an open position facilitating mixture of the first fluid and the second fluid. The release component may be, for example, button 16. When button 16 is activated or depressed, this causes button shaft 17 to move to a second position. Moving to the second position entails button shaft 17 moving downwards such that the shaft serrations of button shaft 17 separate from the door serrations of door 7. Once button shaft 17 is in the second position, in response, door 7 may open. Once door 7 is opened, windowed compartment 202 and inner compartment 13 are no longer separated, and thus, fluid from each of windowed compartment 202 and inner compartment 13 may mix in a newly formed single compartment comprising both windowed compartment 202 and inner compartment 13. In an embodiment, the release component comprises button 16 which houses spring 102. Spring 102 may include at least one compressive element that compresses when button 16 is activated or depressed, causing spring 102 to contact button shaft 17 and move button shaft 17 from the first position to the second position.

While various embodiments have been described above, it should be understood that they have been presented by way of example only, and not of limitation. Likewise, the various diagrams may depict an example architectural or other configuration, which is done to aid in understanding the features and functionality that can be included. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components may be described or claimed in the singular, the plural is contemplated to be within the scope thereof unless limitation to the singular is explicitly stated.

As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:
1. A container, comprising:
a stationary first compartment for holding a first fluid;

a stationary second compartment with an opening for holding a second fluid;

a door for separating the stationary first compartment and the stationary second compartment;

a shaft for holding the door in a closed position when the shaft is in a first position relative to the door; and a release component, coupled to the shaft, for moving the shaft to a second position relative to the door allowing the door to move to an open position;

wherein the door comprises a plurality of door serrations for mating with a plurality of shaft serrations of the shaft to hold the door in the closed position when the shaft is in the first position, and wherein the first fluid and the second fluid mix in response to the door moving to the open position.

2. The container of claim 1, wherein the first compartment is a windowed compartment.

3. The container of claim 1, wherein the plurality of shaft serrations move out of contact with the door serrations when the shaft moves to the second position.

4. The container of claim 1, wherein the door is nontransparent to hide the second compartment holding the second fluid from view.

5. The container of claim 1, wherein the shaft is coupled to the second compartment.

6. The container of claim 1, wherein the shaft moves from the first position to the second position by moving in a downward motion.

7. The container of claim 1, wherein the release component comprises:
 a button; and
 a spring coupled to the button, wherein the spring contacts the shaft when the button is activated, allowing the door to move to the open position.

8. The container of claim 1, wherein the first fluid comprises beads or capsules each comprising a coating and a non-solid or a substantially non-solid substance, wherein (a) the substance is suitable for dermatological application and (b) the coating (i) is at least substantially impervious to the substance under ambient conditions when separated from an aqueous acidic solution and (ii) is degraded, substantially degraded, or becomes liquid permeable when contacted with an acidic aqueous solution.

9. The container of claim 1, wherein the first fluid comprises beads or capsules each capsule including a coating, such as a degradable coating and the second fluid comprises an acid reactive to the degradable coating of the capsules of the first fluid when the first fluid and the second fluid are mixed.

10. A method for preparing a container, comprising:
 inserting a first fluid in a stationary first compartment;
 inserting a second fluid in a stationary second compartment;
 separating the first stationary compartment and the second stationary compartment with a door;
 positioning a shaft in a first position relative to the door to hold the door in a closed position;
 wherein a plurality of shaft serrations of the shaft mate with a plurality of door serrations of the door to retain the door in the closed position when the shaft is in the first position; and
 coupling a release component to the shaft, wherein activation of the release component causes the shaft to move to a second position relative to the door, which causes or allows the door to move to an open position facilitating mixture of the first fluid and the second fluid.

11. The method of claim 10, further comprising:
 activating the release component causing the first fluid and the second fluid to mix.

12. The method of claim 10, wherein the plurality of shaft serrations move out of contact with the door serrations when the shaft moves to the second position.

13. The method of claim 10, wherein coupling a release component to the shaft comprises:
 coupling a spring to the shaft; and
 coupling a button to the spring.

14. The method of claim 13, further comprising:
 activating the button to allow the door to move to the open position.

15. The method of claim 10, wherein the first compartment is a windowed compartment.

16. The method of claim 10, wherein the door is nontransparent to hide the second compartment holding the second fluid from view.

17. The method of claim 10, wherein the shaft is coupled to the second compartment.

18. The method of claim 10, wherein the shaft moves from the first position to the second position by moving in a downward motion.

19. The method of claim 10, wherein the first fluid comprises beads or capsules each comprising a coating and a non-solid or a substantially non-solid substance, wherein (a) the substance is suitable for dermatological application and (b) the coating (i) is at least substantially impervious to the substance under ambient conditions when separated from an aqueous acidic solution and (ii) is degraded, substantially degraded, or becomes liquid permeable when contacted with an acidic aqueous solution.

20. The method of claim 10, wherein the first fluid comprises beads or capsules each capsule including a coating, such as a degradable coating and the second fluid comprises an acid reactive to the degradable coating of the capsules of the first fluid when the first fluid and the second fluid are mixed.

* * * * *